United States Patent
Hoehn et al.

(10) Patent No.: US 8,198,435 B2
(45) Date of Patent: Jun. 12, 2012

(54) CRYSTAL FORM OF N-BENZOYL-STAUROSPORINE

(75) Inventors: Pascale Hoehn, Eschentzwiller (FR); Bernd Koch, Buschwiller (FR); Michael Mutz, Freiburg i. Br. (DE)

(73) Assignee: Novartis AG, Basel (CH)

( * ) Notice: Subject to any disclaimer, the term of this patent is extended or adjusted under 35 U.S.C. 154(b) by 958 days.

(21) Appl. No.: 11/718,029

(22) PCT Filed: Nov. 3, 2005

(86) PCT No.: PCT/EP2005/011789
§ 371 (c)(1),
(2), (4) Date: Apr. 26, 2007

(87) PCT Pub. No.: WO2006/048296
PCT Pub. Date: May 11, 2006

(65) Prior Publication Data
US 2009/0137552 A1    May 28, 2009

Related U.S. Application Data

(60) Provisional application No. 60/625,343, filed on Nov. 5, 2004, provisional application No. 60/642,131, filed on Jan. 7, 2005.

(51) Int. Cl.
*C07D 498/22* (2006.01)
*A61K 31/553* (2006.01)
*A61P 35/04* (2006.01)

(52) U.S. Cl. .................................. 540/545; 514/211.08
(58) Field of Classification Search ............. 514/211.08; 540/545
See application file for complete search history.

(56) References Cited

U.S. PATENT DOCUMENTS
| | | | |
|---|---|---|---|
| 4,107,297 A | 8/1978 | Omura et al. | |
| 5,073,633 A | 12/1991 | Schroeder et al. | |
| 5,093,330 A | * 3/1992 | Caravatti et al. | 514/211.08 |

FOREIGN PATENT DOCUMENTS
| | | |
|---|---|---|
| EP | A-1288212 | 3/2003 |
| JP | 60185719 | 9/1985 |
| RU | 2191175 C2 | 10/2002 |
| WO | WO01/16161 | 3/2001 |
| WO | WO02/076432 | 10/2002 |
| WO | WO 2004/094645 | 11/2004 |

OTHER PUBLICATIONS

"The United States Pharmacopeia, The National Formulary", United States Pharmacopeial Convention, Inc. USP 23, NF 18, (941; X-ray Diffraction), pp. 1843-1844, (Jan. 1, 1995).

Yu L., "Amorphous pharmaceutical solids: preparation, characterization and stabilization", Advanced Drug Delivery Reviews, vol. 48, No. 1, pp. 27-42, (May 16, 2001).

Caira, M.R. "Crystalline Polymorphism of Organic Compounds" in Weber, E,. Et al (Ed), Topics in Current Chemistry, vol. 196, pp. 163-208, (1998).

Yinsheng Yao, Natural Medicine Chemistry, $2^{nd}$ edition, The Peoples Medical Publishing, pp. 459, section 5.1.1.2. (1994) English translation of relevant part.

A. Tenzer et al, "The Phosphalidylinositide 3'-Kinase/Akt Survival Pathway is a Target for the Anticancer and Radiosensitizing Agent PKC412, an Inhibitor of Protein Kinase C1", Cancer Research, vol. 61, pp. 8203-8210 (2001).

J. Chen et al., "PKC412 inhibits the zinc finger 198-fibroblast growth factor receptor 1 fusion tyronise kinase and is active in treatment of stem cell myeloproliferativ disorder", PNAS, vol. 101. No. 40 pp. 14479-14484, (Oct. 5, 2004).

D.J. Propper et al. "Phase I and Pharmacokinetic Study of PKC412, an Inhibitor of Protein Kinase C", Journal of Clinical Oncology, vol. 19, No. 5, pp. 1485-1492, (Mar. 1, 2001).

Aulton, M. Editor,"Pharmaceutics The science of dosage form design", $2^{nd}$ edition, Churchill Livingstone Press, Spain, pp. 142-143, 145, 2002.

* cited by examiner

*Primary Examiner* — Brenda Coleman
(74) *Attorney, Agent, or Firm* — George R. Dohmann (57) ABSTRACT

The invention relates to a new crystalline form II of N-benzoyl-staurosporine; compositions containing the same; processes for the preparation thereof; and the use of crystalline form II of N-benzoyl-staurosporine in diagnostic methods or therapeutic treatment of warm-blooded animals, especially humans. The invention relates to the amorphous forms of N-benzoyl-staurosporine; compositions containing the same; processes for the preparation thereof; and the use of amorphous N-benzoyl-staurosporine in diagnostic methods or therapeutic treatment of warm-blooded animals, especially humans.

16 Claims, 4 Drawing Sheets

CRYSTAL FORM OF N-BENZOYL-STAUROSPORINE

This application is the National Stage of Application No. PCT/EP2005/011789, filed on Nov. 3, 2005, which claims benefit under 35 U.S.C. §119(e) of U.S. Provisional Application No. 60/625,343, filed Nov. 5, 2004 and U.S. Provisional Application No. 60/642,131 filed Jan. 7, 2005. The contents of both are incorporated herein by reference in their entirety.

The invention relates to a new crystalline form II of N-benzoyl-staurosporine, the process for preparation of the crystalline form II of N-benzoyl-staurosporine, compositions containing crystalline form II of N-benzoyl-staurosporine, and the use of crystalline form II of N-benzoyl-staurosporine in diagnostic methods or therapeutic treatment of warm-blooded animals, especially humans.

The invention relates to amorphous N-benzoyl-staurosporine, the process for the preparation of amorphous N-benzoyl-staurosporine, compositions containing amorphous of N-benzoyl-staurosporine, and the use of amorphous N-benzoyl-staurosporine in diagnostic methods or therapeutic treatment of warm-blooded animals, especially humans.

BACKGROUND OF THE INVENTION

The drug N-benzoyl-staurosporine is used as an anti-tumour agent. In general, the preparation of N-benzoyl-staurosporine is known in the art. However, it is also known that different polymorphic forms of the same drug may have substantial differences in certain pharmaceutically important properties. Therefore, there is a continuing need for new solid forms of N-benzoyl-staurosporine and new methods of preparation.

SUMMARY OF THE INVENTION

In accordance with one aspect, the invention provides a crystalline form II of N-benzoyl-staurosporine. Preferably, the crystalline form II of N-benzoyl-staurosporine has an X-ray diffraction pattern with a peak at an angle of refraction 2-theta ($\theta$) of 8.7±0.2 as depicted in FIG. 1.

Figure 1:
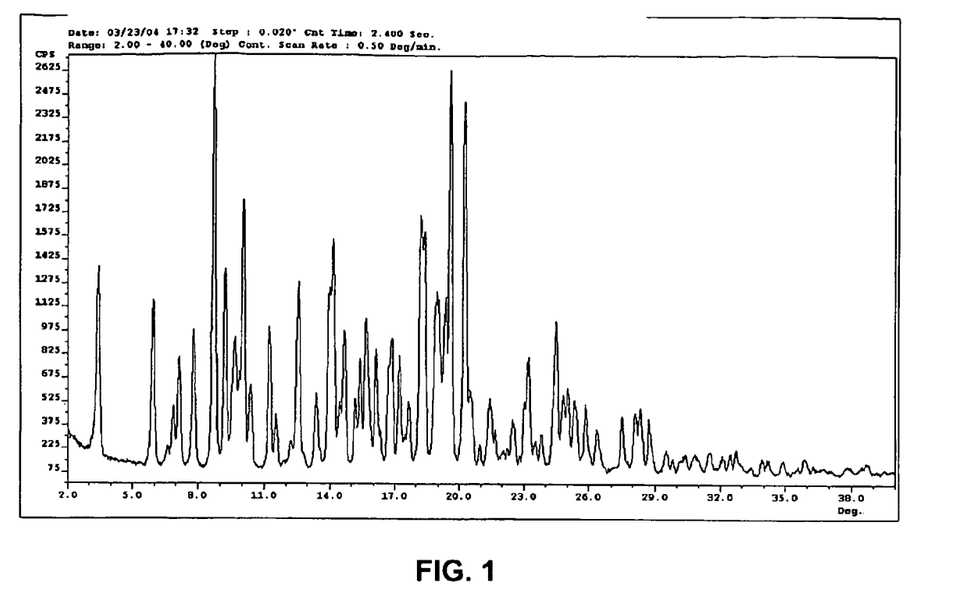
FIG. 1 shows the X-ray powder diffraction diagram of crystalline form II of N-benzoyl-staurosporine.

In accordance with yet another aspect, the invention provides a composition that contains N-benzoyl-staurosporine in a solid form, wherein at least 80% by weight of the solid N-benzoyl-staurosporine is its crystalline form II having an X-ray diffraction pattern with a peak at an angle of refraction $2\theta$ of 8.7±0.2 as depicted in FIG. 1. Various embodiments and variants are provided.

In accordance with yet another aspect, the invention provides a pharmaceutical composition that includes crystalline form II of N-benzoyl-staurosporine and a pharmaceutically acceptable carrier or diluent. Preferably, the pharmaceutical composition is for oral administration.

In accordance with yet another aspect, the invention also relates to amorphous N-benzoyl-staurosporine, the process for the preparation of amorphous N-benzoyl-staurosporine and compositions containing amorphous N-benzoyl-staurosporine.

In accordance with another aspect, the invention provides a pharmaceutical composition that includes a prophylactically or therapeutically effective amount of amorphous N-benzoyl-staurosporine and one or more pharmaceutically acceptable excipients. The pharmaceutical compositions of this aspect of the invention may be formulated, e.g., for oral administration.

In accordance with yet another aspect, the invention provides processes for purifying staurosporine.

In accordance with yet another aspect, the invention provides a process for the preparation of N-benzoyl-staurosporine by reacting staurosporine with benzoic anhydride. This process optionally further comprises seeding the reaction solution to produce either amorphous or crystalline form II of N-benzoyl-staurosporine.

In accordance with yet another aspect, the invention provides a process for the preparation of amorphous N-benzoyl-staurosporine involving spray drying a solution containing N-benzoyl-staurosporine.

Pharmaceutical compositions that include a prophylactically or therapeutically effective amount of amorphous N-benzoyl-staurosporine produced by the process described, and one or more pharmaceutically acceptable excipients are also provided.

In accordance with yet another aspect, the invention provides a process for making the crystalline form II of N-benzoyl-staurosporine, the process including:
(a) providing a solution of N-benzoyl-staurosporine in either a protic or an aprotic solvent;
(b) seeding with the crystalline form II of N-benzoyl-staurosporine and contacting the reaction mixture with an alcohol solvent to form a precipitate; and
(c) isolating the precipitate, which is the crystalline form II of N-benzoyl-staurosporine. Various embodiments and variants are provided.

DETAILED DESCRIPTION OF THE INVENTION

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

For the purposes of the present invention, the following terms are defined below.

The crystalline compound, designated herein as "crystalline form II" and referred to hereinafter as crystalline form II of N-benzoyl-staurosporine. It is characterized via X-ray powder diffraction, and/or infrared spectroscopy. It is further described below.

"Pharmaceutically acceptable" means that which is useful in preparing a pharmaceutical composition that is generally non-toxic and is not biologically undesirable and includes that which is acceptable for veterinary use and/or human pharmaceutical use.

"Anti-solvent" is a solvent which when added to an existing solution of a substance reduced the solubility of the substance.

The term "composition" includes, but is not limited to, a powder, a solution, a suspension, a gel, an ointment, an emulsion and/or mixtures thereof. The term composition is intended to encompass a product containing the specified ingredients in the specified amounts, as well as any product, which results, directly or indirectly, from combination of the specified ingredients in the specified amounts. A "composition" may contain a single compound or a mixture of compounds. A "compound" is a chemical substance that includes molecules of the same chemical structure.

The term "pharmaceutical composition" is intended to encompass a product comprising the active ingredient(s), pharmaceutically acceptable excipients that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing the active ingredient, additional active ingredient(s) and pharmaceutically acceptable excipients.

The term "excipient" means a component of a pharmaceutical product that is not the active ingredient, such as filler, diluent and carrier. The excipients that are useful in preparing a pharmaceutical composition are preferably generally safe, non-toxic and neither biologically nor otherwise undesirable, and are acceptable for veterinary use, as well as human pharmaceutical use. "A pharmaceutically acceptable excipient", as used in the specification and claims, includes both one and more than one such excipient.

"Therapeutically effective amount" means the amount of a compound that, when administered for treating or preventing a disease, is sufficient to effect such treatment or prevention for the disease. The "therapeutically effective amount" will vary depending on the compound, the disease and its severity and the age, weight, etc., of the patient to be treated.

When referring to a chemical reaction, the terms "treating", "contacting" and "reacting" are used interchangeably herein and refer to adding or mixing two or more reagents under appropriate conditions to produce the indicated and/or desired product. It should be appreciated that the reaction which produces the indicated and/or desired product may not necessarily result directly from the combination of two reagents which were initially added, i.e., there may be one or more intermediates which are produced in the mixture which ultimately leads to the formation of the indicated and/or desired product.

The term "substantially free of" in reference to a composition, as used herein, means that the substance form which the composition is free of cannot be detected by methods known to those skilled in the art.

Figure 3:
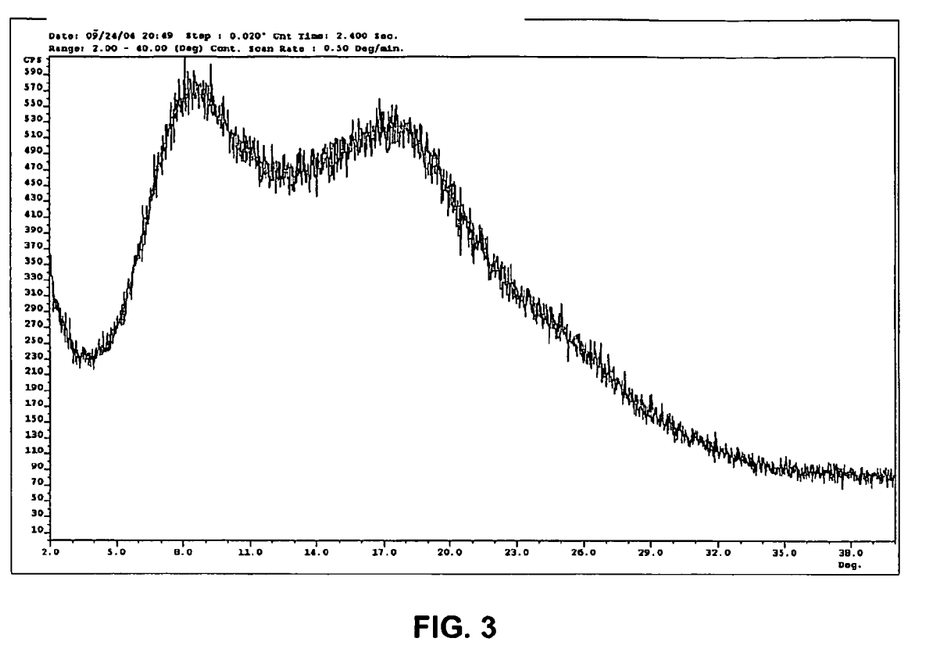
FIG. 3 shows the X-ray powder diffraction diagram of a purely amorphous form of N-benzoyl-staurosporine.
Figure 4:
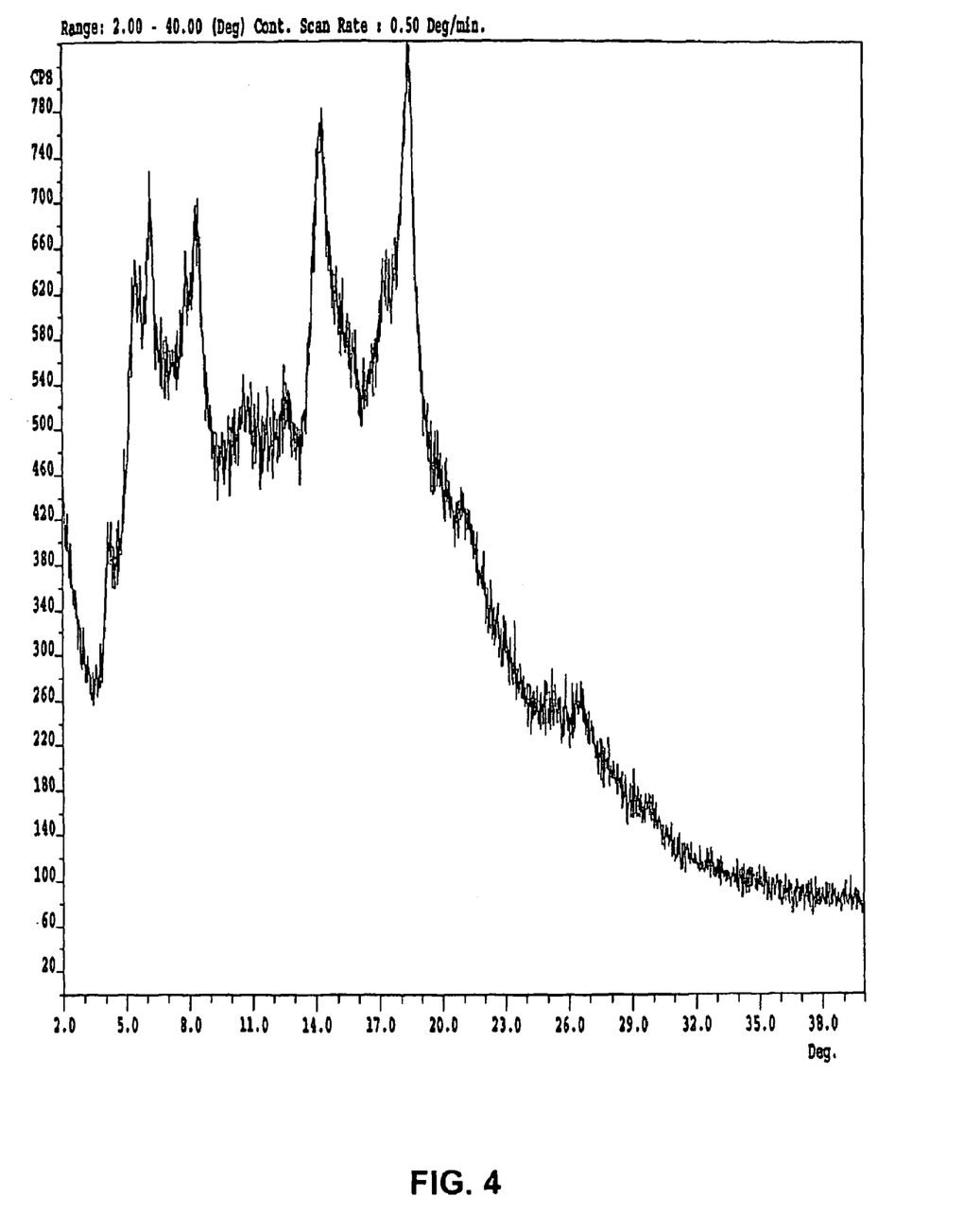
FIG. 4 shows the X-ray powder diffraction diagram of an essentially amorphous form of N-benzoyl-staurosporine.

The term "amorphous" means a material that may be substantially free of crystalline impurities, or contain substantial amounts of crystalline impurities. Amorphous material containing substantial amounts of crystalline materials as impurities is hereby referred to as "N-benzoyl-staurosporine essentially amorphous". As illustrated in FIG. 4, the presence of crystalline impurities does not allow for a good halo shape pattern typical of amorphous form that is substantially free of crystalline material. The amorphous material that is substantially free of crystalline forms is hereby referred to as "N-benzoyl-staurosporine purely amorphous". FIG. 3 illustrates an X-ray diffractogram pattern for this form, where the halo shape of the pattern illustrates the substantial absence of crystalline structure. Peaks are particularly missing in the regions characteristics of crystalline form.

The examples further illustrate processes for obtaining both "N-benzoyl-staurosporine essentially amorphous" and "N-benzoyl-staurosporine purely amorphous".

N-benzoyl-staurosporine is known as (9α,10β,11β,13α)-N-(2,3,10,11,12,13-hexahydro-10-methoxy-9-methyl-1-oxo-9,13-epoxy-1h, 9H-diindolo[1,2,3-gh:3',2',1'-1 m]pyrrolo[3,4-j][1,7]benzodiazonin-11-yl)-N-methyl-benzamide) and has the following chemical structure:

(I)

U.S. Pat. No. 5,093,330 (the '330 patent), incorporated herein by reference in its entirety, claims N-benzoyl-staurosporine. The invention relates especially to a particular form preferably that which is referred to hereinafter as crystalline form II of a N-benzoyl-staurosporine derivative of the compound of formula (I), described above, and to the amorphous forms of N-benzoyl-staurosporine.

Different solid forms of the same drug may exhibit different properties, including characteristics that have functional implications with respect to their use as drug may have substantial differences in such pharmaceutically important properties as dissolution rates and bioavailability. Likewise, different polymorphs may have different processing properties, such as hydroscopicity, flowability and the like, which could affect their suitability as active pharmaceuticals for commercial production.

X-ray powder diffraction patterns was measured on a Scintag INC X 1 using the Bragg-Brentano parafocusing geometry. The X-ray diffraction pattern depicted in FIG. 1 is summarized in Table 1.

TABLE 1

Powder X-Ray Diffraction Peaks for the Form II
Crystal Modification of N-benzoyl-staurosporine

| 2 θ (deg) | d-spacing (Å) | Relative intensity |
|---|---|---|
| 3.4 | 26.1 | medium |
| 6.0 | 14.8 | medium |
| 7.8 | 11.3 | medium |
| 8.7 | 10.1 | strong |
| 9.2 | 9.6 | medium |
| 9.7 | 9.1 | medium |
| 10.1 | 8.8 | medium |
| 10.4 | 8.5 | low |
| 11.2 | 7.9 | medium |
| 12.6 | 7.0 | medium |
| 14.1 | 6.3 | medium |
| 15.7 | 5.7 | medium |
| 16.8 | 5.3 | medium |
| 18.2 | 4.9 | medium |
| 18.9 | 4.7 | medium |
| 19.3 | 4.6 | medium |
| 19.6 | 4.5 | strong |
| 20.2 | 4.4 | strong |
| 24.5 | 3.6 | medium |

It should be kept in mind that slight variations in observed 2θ angles or spacing values are expected based on the specific diffractometer employed, the analyst and the sample preparation technique. More variation is expected for the relative peak intensities. Identification of the exact crystalline form of a compound should be based primarily on observed 2θ angles with lesser importance attributed to relative peak intensities.

Some margin of error is present in each of the 2θ angle assignments reported herein. The assigned margin of error, in a preferred variant, the crystalline form II of N-benzoyl-staurosporine is approximately ±0.2 for each of the peak assignments.

Figure 2:
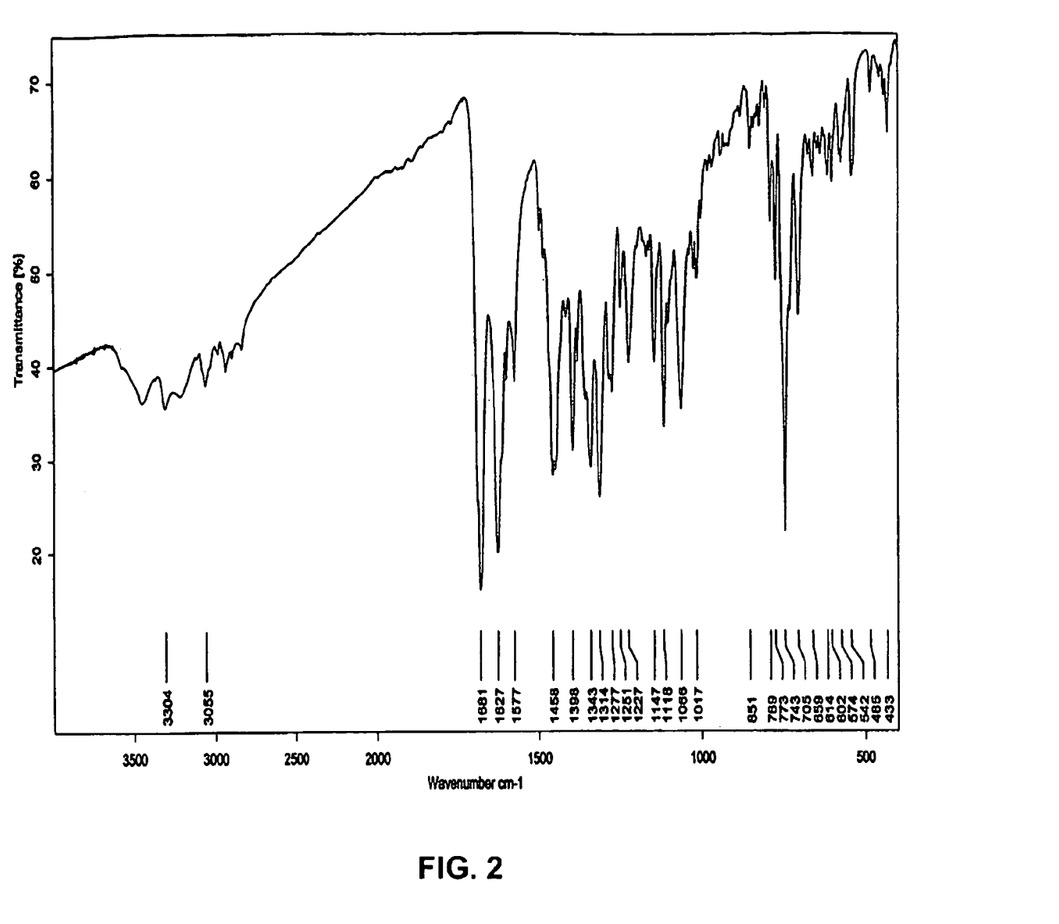
FIG. 2 shows a characteristic infrared spectrum of crystalline form II of N-benzoyl-staurosporine.

The crystalline form II of N-benzoyl-staurosporine may be also characterized by infrared spectroscopy. The crystalline form II exhibits a characteristic absorption pattern in infrared (IR) spectroscopic analysis as depicted in FIG. 2. IR spectroscopic analysis was measured on a Bruker IFS-55. The crystalline form II of N-benzoyl-staurosporine has characteristic absorptions, which can be distinguished from that of other polymorphs, at about 789, 773, 743, 704, 1066, 1026, 1458, 1398, 1383, 1602, 1577, 1497, 1627, 1680, 2934 and 3055 $cm^{-1}$ in IR spectroscopic analysis. Some margin of error is present in each of the characteristic absorptions reported herein. The assigned margin of error in the characteristic absorptions is approximately 2 $cm^{-1}$ in the range of 1900-800 $cm^{-1}$.

One or more of physical properties and/or spectroscopic properties can be the basis for characterizing the crystal or polymorphic forms of N-benzoyl-staurosporine.

The invention also provides a composition containing solid N-benzoyl-staurosporine, which is at least 80%, by total weight of the solid N-benzoyl-staurosporine in the composition, its crystalline form II. The preferred form of this composition is solid N-benzoyl-staurosporine powder suitable for use as active ingredient in formulating pharmaceutical products. The remainder of the solid N-benzoyl-staurosporine in the composition, i.e., 20% or less of the total weight of N-benzoyl-staurosporine may be, e.g., other crystalline forms of N-benzoyl-staurosporine. In one specific embodiment, the composition contains at least 90% of the crystalline form II of N-benzoyl-staurosporine with respect to the total weight of the solid N-benzoyl-staurosporine in the composition. In another specific embodiment, the composition contains at least 95% of the crystalline form II with respect to total weight of the solid N-benzoyl-staurosporine in the composition.

In another aspect, the invention also provides processes for purifying staurosporine. While the invention is not limited to any specific theory, the inventors found that a process involves:
(a) providing a suspension of staurosporine in an alcohol solvent;
(b) contacting the suspension with methanesulfonic acid to get a solution;
(c) further contacting the solution with triethylamine; and
(d) isolating the product.

The process further comprises washing the product in a protic or aprotic solvent. A non-limiting example of a protic solvent is ethanol and a non-limiting example of an aprotic solvent is tetrahydrofuran (THF). The invention also provides a process for:
(a) providing a solution of crude staurosporine in either a protic or aprotic solvent
(b) seeding the solution with purified staurosporine;
(c) contacting the reaction mixture with an alcohol solvent to form a precipitate; and
(d) isolating the product which is the purified staurosporine.

After the starting material is purified, the material may be converted to either the crystalline form II or amorphous N-benzoyl-staurosporine. The material may be converted to the crystalline form II of N-benzoyl-staurosporine, the process comprising:
(a) reacting staurosporine in an alcohol solvent, such as ethanol, with benzoic anhydride; and
(b) seeding the reaction solution with crystalline form II of N-benzoyl-staurosporine to produce the product
(c) isolating the product which is crystalline form II of N-benzoyl-staurosporine.

The material may be converted to amorphous N-benzoyl-staurosporine by:
(a) reacting staurosporine in a solvent, such as ethanol or THF, with benzoic anhydride; and
(b) seeding the reaction with amorphous N-benzoyl-staurosporine to produce the product.
(c) isolating the product which is amorphous N-benzoyl-staurosporine.

The product may be further washed with the solvent multiple times to produce N-benzoyl-staurosporine essentially amorphous.

The technique of spray drying may also be used to prepare N-benzoyl-staurosporine purely amorphous.

B4

B4

IP-Process
Crystallisation
in Benzyl alcohol
and Ethanol

The invention also provides a composition containing N-benzoyl-staurosporine essentially amorphous. The invention also provides a composition containing N-benzoyl-staurosporine purely amorphous.

A process for the preparation of crystalline form II of N-benzoyl-staurosporine is also provided. The process involves:

(a) providing a solution of N-benzoyl-staurosporine in either a protic or aprotic solvent;

(b) seeding the solution with crystalline form II of N-benzoyl-staurosporine;

(c) contacting the suspension with an alcohol solvent to form a precipitate; and (d) isolating the precipitate, which is the crystalline form II of N-benzoyl-staurosporine.

Non-limiting examples of the protic or aprotic solvents are listed in the Table below:

EXAMPLES

Benzyl Alcohol
Ethanol
Dimethyl Sulfoxide (DMSO)
Dimethyl formamide (DMF)
THF
Acetic acid
Polyethylene glycol (PEG 200)

The peaks of the X-ray powder diffractogram of crystalline form II that are of medium to low strength obtained from the above identified solvents can show some variations due to the presence of different solvent molecules within the crystal lattice structure.

In one embodiment, N-benzoyl-staurosporine is dissolved in benzyl alcohol, precipitated by addition of seeding crystals of the crystalline form II of N-benzoyl-staurosporine and addition of ethanol as the anti-solvent, and crystalline form II of N-benzoyl-staurosporine is obtained. This process is highly-reproducible and the resulting crystalline product has good filtration. The residual solvent content in B6 is around 4.3% wt/wt of benzyl alcohol and 0.5-1% wt/wt of ethanol. The process is shown schematically as:

B6

The above conditions on the selective preparation of the individual crystal forms are not conclusive. In general, e.g., it is possible to vary parameters such as the weight ratio of the compound of formula (I) to the solvent and anti-solvent.

Also provided are pharmaceutical compositions containing a crystalline form II or amorphous N-benzoyl-staurosporine and a pharmaceutically acceptable carrier. In addition to the active compound, the pharmaceutical composition include one or more pharmaceutically acceptable carriers, also known as excipients, which ordinarily lack pharmaceutical activity, but have various useful properties which may, e.g., enhance the stability, sterility, bioavailability and ease of formulation of a pharmaceutical composition. These carriers are pharmaceutically acceptable, meaning that they are not harmful to humans or animals when taken appropriately and are compatible with other ingredients in a given formulation. The carriers may be solid, semi-solid or liquid, and may be formulated with the compound in bulk, but ultimately in the form of a unit-dose formulation, i.e., a physically discrete until containing a specific amount of active ingredient, such as a tablet or capsule. The pharmaceutical compositions may include, in addition to a compound of this invention, one or more active pharmaceutical compounds.

The pharmaceutical compositions may be in the form of suspensions, solutions, elixirs, aerosols or solid dosage forms.

The pharmaceutical compositions are contemplated in various formulations suitable for various modes of administration including, but not limited to, inhalation, oral, rectal, parenteral (including subcutaneous, intradermal, intramuscular and intravenous), implantable and transdermal administration. The most suitable route of administration in an given case depends on the duration of the subject's condition, the length of treatment desired, the nature and severity of the condition being treated, and the particular formulation that is being used. The formulations may be in bulk or in unit dosage form, and may be prepared by methods well-known in the art for a given formulation.

The amount of active ingredient included in a unit dosage form depends on the type of formulation in which the active ingredient is presented. A pharmaceutical composition will generally contain about 0.1% by weight to about 99% by weight of the active ingredient, preferably about 1% by weight to 50% by weight for oral administration and about 0.2% by weight to about 20% by weight for parenteral administration.

Formulations suitable for oral administration include capsules (hard and soft), cachets, lozenges, syrups, suppositories and tablets, each containing a predetermined amount of the active compound; as a powder or granules, as a solution or a suspension in an aqueous or non-aqueous liquid; or as an oil-in-water or water-in-oil emulsion. Such formulations may be prepared by any suitable method of pharmacy that includes the step of bringing into association the active compound and a suitable carrier or carriers. The amount of active ingredient per unit dosage of solid formulations may be as described in prior art for preparations of N-benzoyl-staurosporine.

In another aspect, the invention also provides methods of treatment using the compounds and the pharmaceutical compositions of this invention. The compounds and compositions of this invention may be administered to a subject in an amount effective to be used for treatment and prevention of the conditions disclosed in the '330 patent. By subject is meant a human or an animal, preferably human. Animals contemplated by this invention include any animal safely treatable by compounds of this invention. Most notably, the crystalline form II and amorphous N-benzoyl-staurosporine show high anti-proliferative and anti-tumor activity, as a result of Protein Kinase C (PKC) inhibition, which may be extremely useful for cancer treatment. Moreover, their highly selective and potent inhibition of PKC may lead to superior clinical outcomes for the patient, i.e., delay or suppress disease progression, with equally tolerable regimens. Potential applications include a variety of solid tumors and more specifically for example breast cancer, colon cancer, ovarian cancer and leukemia. In addition, various other indications that may be affected by PKC activity may be effectively treated by these compositions, including multidrug resistance (MDR), one of the major problems in currently employed cancer chemotherapy and inflammatory diseases in general.

The present invention relates especially to crystalline form II and amorphous N-benzoyl-staurosporine disclosed herein for the treatment of one of the said diseases or in the preparation of a pharmacological agent for the treatment thereof.

The invention relates also to a process for the treatment of warm-blooded animals suffering from said diseases, especially a tumor disease, wherein a quantity of the crystalline form II or amorphous N-benzoyl-staurosporine, which is effective against the disease concerned, especially a quantity with anti-proliferative and especially tumor-inhibiting efficacy, is administered to warm-blooded animals in need of such treatment. The invention relates moreover to the use of the crystalline form II or amorphous N-benzoyl-staurosporine for the inhibition of the above-mentioned PKC, or for the preparation of pharmaceutical compositions for use in treating the human or animal body, especially for the treatment of a variety of solid tumors and more specifically, e.g., breast cancer, colon cancer, ovarian cancer and leukemia. Depending on species, age, individual condition, mode of administration and the clinical picture in question, effective doses, e.g., daily doses of about 1-2500 mg, preferably 1-1000 mg, especially 5-500 mg, are administered to warm-blooded animals of about 70 kg body weight.

The invention relates also to pharmaceutical preparations which contain an effective amount, especially an effective amount for prevention or treatment of one of the said diseases, of the crystalline form II or amorphous N-benzoyl-staurosporine of formula (I), together with pharmaceutically acceptable carriers which are suitable for topical; enteral, e.g., oral or rectal; or parenteral administration and may be inorganic or organic and solid or liquid. Especially tablets or gelatin capsules containing the active substance together with diluents, e.g., lactose, dextrose, sucrose, mannitol, sorbitol, cellulose and/or glycerin; and/or lubricants, e.g., silica, talc, stearic acid or salts thereof, typically magnesium or calcium stearate; and/or PEG, are used for oral administration. Tablets may likewise contain binders, e.g., magnesium aluminum silicate, starches, typically corn, wheat or rice starch, gelatin, methylcellulose, sodium carboxymethylcellulose and/or polyvinylpyrrolidone; and, if so desired, disintegrants, e.g., starches, agar, alginic acid or a salt thereof, typically sodium alginate; and/or effervescent mixtures, or adsorbents, coloring agents, flavors and sweetening agents. The pharmacologically active compounds of the present invention may further be used in the form of preparations for parenteral administration or infusion solutions. Such solutions are preferably isotonic aqueous solutions or suspensions, these possibly being prepared before use, e.g., in the case of lyophilised preparations containing the active substance either alone or together with a carrier, e.g., mannitol. The pharmaceutical substances may be sterilised and/or may contain excipients, e.g., preservatives, stabilisers, wetting agents and/or emulsifiers; solubilizers; salts for the regulation of osmotic pressure; and/or buffers. The present pharmaceutical preparations which, if so desired, may contain further pharmacologically active substances, such as antibiotics, are prepared in a manner known per se, e.g., by means of conventional mixing, granulating, coating, dissolving or lyophilising processes, and contain from about 1-100%, especially from about 1% to about 20%, of the active substance or substances.

The invention is further defined by reference to the following examples describing in detail the preparation of the compound and the compositions of the present invention, as well as their utility. It will be apparent to those skilled in the art, that many modifications, both to materials, and methods, may be practiced with out departing from the purpose and interest of this invention. The examples that follow are not intended to limit the scope of the invention as defined hereinabove or as claimed below.

EXAMPLES

Example 1

Purification of Staurosporine B1 to Staurosporine B2 Using Methanesulfonic Acid and Triethylamine A reactor is charged with staurosporine B1 and ethanol. The suspension is heated to about 70° C. Methanesulfonic acid is added to the suspension and the obtained solution is aged. Activated charcoal and Hyflo are added and the mixture is aged. The suspension is filtered and the filter apparatus and filter cake are washed multiple times with ethanol. The clear filtered solution is transferred to another reactor and cooled to about 60° C. Triethylamine diluted in ethanol is added slowly to the reaction mixture. Afterwards, the suspension is cooled to about 20° C. and aged. The staurosporine B2 is isolated by filtration. The product is rinsed multiple times with ethanol.

Example 2

Purification of Crude Staurosporine B1 to Staurosporine B2 Through Crystallization A reactor is charged with staurosporine B1 and benzyl alcohol. The suspension is heated to about 85° C. and aged. Activated charcoal and Hyflo are added to the solution and the mixture is aged again. The suspension is filtered at about 90° C. The filter apparatus and filter cake are washed multiple times with benzyl alcohol. The clear filtered solution is transferred to another reactor and cooled to about 70° C. The solution is seeded with staurosporine B2 suspended in ethanol. Afterwards, ethanol is added to the suspension and the suspension is aged, then cooled to about 0° C. The suspension is again aged for at least 2 hours at about 0° C. The staurosporine B2 is isolated by filtration. The product is rinsed multiple times with ethanol.

Example 3

Benzylation of Staurosporine B2 to Prepare Essentially Amorphous N-Benzoyl-Staurosporine A reactor is charged with staurosporine B2 with benzoic anhydride, ethanol and water. The reaction mixture is heated to about 70° C. and aged. The solution is filtered and the filter apparatus and filter cake are washed multiple times with ethanol. The filtered solution is transferred to another reactor and cooled to about 60° C. Water is slowly added to the solution. The solution is seeded with amorphous N-benzoyl-staurosporine. The suspension is aged, then cooled to about 20° C. then aged again. N-benzoyl-staurosporine is isolated by filtration. The wet cake of N-benzoyl-staurosporine is rinsed multiple times with absolute ethanol. The wet cake is then re-suspended in the filter apparatus in ethanol, aged at about 25° C. then cooled to about 0-5° C. and aged again. This process step may be repeated multiple times. N-benzoyl-staurosporine is isolated by filtration. The wet cake is dried in a vacuum oven at an external temperature of about 40° C. and a vacuum of approximately 10-20 mbar for about 24 hours to obtain product: 35-40 g dried cake: 27 g theory quell. Yield: approximately 82% of theory quell related to B1 100%.

The use of ethanol in the above reaction may be replaced with THF.

Example 4

Benzylation of Staurosporine B2 to Prepare Crystalline Form II of N-Benzoyl-Staurosporine B4

A reactor is charged with staurosporine B2 with benzoic anhydride, absolute ethanol and water. The reaction mixture is heated to about 70° C. and aged. At the end of the reaction time, the reaction mixture is seeded with crystalline form II of N-benzoyl-staurosporine suspended in absolute ethanol. After aging, absolute ethanol and water are slowly added to the suspension. The suspension is aged again, then cooled to about 0° C. before crystalline form II of N-benzoyl-staurosporine is isolated by filtration. The wet cake of N-benzoyl-staurosporine is rinsed multiple times with absolute ethanol and then dried in a vacuum oven at an external temperature of 60° C. and a vacuum of approximately 5-30 mbar for about 16 hours to obtain the product: 39.70 g, dried cake: 27.2 g theory quell. Yield: approximately 91.5% of theory quell related to B1 100%.

Example 5

Preparation of Crystalline Form II of N-Benzoyl-Staurosporine Using Benzyl Alcohol and Ethanol A reactor is charged with crude N-benzoyl-staurosporine and benzyl alcohol. The mixture is heated to 85° C. and the solution is subsequently aged. The solution is cooled to about 70° C. then seeded with purified crystalline form II of N-benzoyl-staurosporine B6 suspended in ethanol. Afterwards, ethanol is added and the suspension is aged, then cooled to about 0° C. before crystalline form II of N-benzoyl-staurosporine is isolated by filtration. The wet cake is rinsed with ethanol multiple times and dried.

Example 6

Preparation of Crystalline Form II of N-Benzoyl-Staurosporine Using Acetic Acid and Ethanol A reactor is charged with crude N-benzoyl-staurosporine and acetic acid. The mixture is heated to about 70° C. and the solution is subsequently aged. The solution is then seeded with purified crystalline form II of N-benzoyl-staurosporine B6 suspended in ethanol. Afterwards, ethanol is added to the suspension and the suspension is aged, then cooled to about 20° C. before crystalline form II of N-benzoyl-staurosporine is isolated by filtration. The wet cake is rinsed with ethanol multiple times and dried.

Example 7

Preparation of Crystalline Form II Crystal of N-Benzoyl-Staurosporine Using PEG A reactor is s charged with crude N-benzoyl-staurosporine and PEG. The mixture is heated to about 90° C. and the solution is subsequently aged. The solution is cooled to about 70° C. and seeded with purified crystalline form II of N-benzoyl-staurosporine B6 suspended in ethanol. Afterwards ethanol/water in a 1:1 ratio is slowly added and the suspension is then aged before being cooled to 20° C. The crystalline form II of N-benzoyl-staurosporine is isolated by filtration. The wet cake is rinsed with ethanol multiple times and dried.

Example 8

Preparation of Crystalline Form II of N-Benzoyl-Staurosporine Using DMSO

A reactor is charged with N-benzoyl-staurosporine and DMSO. The mixture is heated to about 70° C. and the solution is subsequently aged then seeded with purified crystalline form II of N-benzoyl-staurosporine B6 suspended in ethanol. Afterwards, ethanol is added to the suspension and the suspension is aged at 70° C., then cooled to about 20° C. The suspension is aged again before crystalline form II of N-benzoyl-staurosporine is isolated by filtration. The product is rinsed with ethanol multiple times and dried.

Example 9

Preparation of Crystalline Form II of N-Benzoyl-Staurosporine Using DMF

A reactor is charged with N-benzoyl-staurosporine and DMF. The mixture is heated to about 70° C., aged and then seeded with purified crystalline form II of N-benzoyl-staurosporine B8 in ethanol. Afterwards, ethanol is added to the suspension and the suspension is aged at about 70° C. then cooled to about 20° C. The suspension is again aged before the crystalline form II of N-benzoyl-staurosporine is isolated by filtration. The product is rinsed with ethanol multiple times and dried.

Example 10

Preparation of Crystalline Form II of N-Benzoyl-Staurosporine Using THF

A reactor is charged with amorphous N-benzoyl-staurosporine and THF. The mixture is heated to about 65° C., aged and then seeded with crystalline form II of N-benzoyl-staurosporine B6 in THF. The suspension is aged, then cooled to about 20° C. and again aged before crystalline form II of N-benzoyl-staurosporine is isolated by filtration. The product is rinsed multiple times with THF and dried.

Example 11

Preparation of Crystalline Form II of N-Benzoyl-Staurosporine Using Ethanol

A reactor is charged with amorphous N-benzoyl-staurosporine and ethanol. The mixture is heated to about 70° C., aged and then seeded with crystalline form II of N-benzoyl-staurosporine B6 in ethanol. The suspension is aged, the cooled to about 20° C. and again aged before crystalline form II of N-benzoyl-staurosporine is isolated by filtration. The product is rinsed multiple times with ethanol and dried.

Example 12

Spray Drying Experiment to Get Amorphous PKC412

The feed solution is prepared by dissolving 10 g of PKC412 (crystalline form II) in approximately 160 g of dichloromethane. The feed is ready to be atomized into droplets from which the organic solvent is evaporated in the drying chamber by heated nitrogen resulting in the formation of amorphous PKC412. The inlet temperature is set to 60° C. whereas the outlet temperature is set to 40° C. The residual solvent content after spray drying was approximately 1% w/w. PKC412 is further dried under vacuum to get a solvent free material.

Example 13

Spray Drying Experiment to Get Amorphous PKC412

The feed solution was prepared by dissolving 7 g of PKC412 (crystalline form II) in approximately 400 g of THF. The feed is ready to be atomized into droplets from which the organic solvent is evaporated in the drying chamber by heated nitrogen resulting in the formation of amorphous PKC412. The inlet temperature is set to 110-120° C. whereas the outlet temperature is set to 70-80° C. The residual solvent content after spray drying is approximately 3% w/w. PKC412 is further dried under vacuum to get a solvent free material.

Example 14

Spray Drying Experiment to Get Amorphous PKC412

The feed solution is prepared by dissolving 7 g of PKC412 (crystalline form II) in approximately 350 g of ethanol/acetic acid 70:30 w/w. The feed is ready to be atomized into droplets from which the organic solvent is evaporated in the drying chamber by heated nitrogen resulting in the formation of amorphous PKC412. The inlet temperature is set to 215° C. whereas the outlet temperature is set to 120° C. The residual solvent content after spray drying is below 0.5%. Further conventional drying is not required.

Example 15

Tablets with Crystalline Form II of N-Benzoyl-Staurosporine

Tablets containing 100 mg of the active substance named in the title are usually prepared in the following composition:

| Composition | Amount (mg) |
| --- | --- |
| Active ingredient | 100 |
| Crystalline lactose | 240 |
| Avicel | 80 |
| PVPPXL | 20 |
| Aerosil | 2 |
| Magnesium stearate | 5 |
| Total | 447 |

Preparation: The active substance is mixed with carrier materials and compressed on a tableting machine (Korsch EKO, punch diameter 10 mm).
Avicel is microcrystalline cellulose (FMC, Philadelphia, USA).
PVPPXL is polyvinylpolypyrrolidone, cross-linked (BASF, Germany).
Aerosil is silicon dioxide (Degussa, Germany).

Example 16

Capsules with Crystalline Form II of N-Benzoyl-Staurosporine

Capsules containing 100 mg of the compound named in the title as active substance are usually prepared in the following composition:

| Composition | Amount (mg) |
| --- | --- |
| Active ingredient | 100 |
| Avicel | 200 |
| PVPPXL | 15 |

-continued

| Composition | Amount (mg) |
|---|---|
| Aerosil | 2 |
| Magnesium stearate | 1.5 |
| Total | 318.5 |

The capsules are prepared by mixing the components and filling the mixture into hard gelatin capsules, size 1.

What is claimed is:

1. A compound which is a crystalline form II of N-benzoyl-staurosporine, which shows on X-ray diffraction a peak at an angle of refraction 2-theta (θ), of 8.7±0.2 degrees.

2. The compound according to claim 1, having an x-ray diffraction pattern, expressed in terms of 2θ angles, that includes five or more peaks selected from the group consisting of about 3.4, 6.0, 7.8, 8.7, 9.2, 9.7, 10.1, 10.4, 11.2, 12.6, 14.1, 15.7, 16.8, 18.2, 18.9, 19.3, 19.6, 20.2 and 24.5±0.2 degrees.

3. The compound according to claim 1, having substantially the same X-ray diffraction pattern as shown in FIG. 1.

4. The compound according to claim 1, which remains dry at 95% relative humidity and 25° C.

5. The compound according to claim 1, having an infrared absorption spectrum with absorption bands at about 789, 773, 743, 704, 1066, 1026, 1458, 1398, 1383, 1602, 1577, 1497, 1627, 1680, 2934 and 3055 cm$^{-1}$±2 cm$^{-1}$.

6. A composition comprising N-benzoyl-staurosporine as a solid, wherein at least 80% by weight of said solid N-benzoyl-staurosporine its crystalline form II according to claim 1.

7. The composition according to claim 6, wherein at least 90% by weight of said solid N-benzoyl-staurosporine is the crystalline form II according to claim 1.

8. The composition according to claim 6, wherein at least 95% by weight of said solid N-benzoyl-staurosporine is the crystalline form II according to claim 1.

9. A pharmaceutical composition in solid form comprising:
    (a) the crystalline form II of N-benzoyl-staurosporine of claim 1; and
    (b) a pharmaceutically acceptable carrier or diluent.

10. The pharmaceutical composition according to claim 9, further comprising one or more pharmaceutically acceptable excipients.

11. The pharmaceutical composition according to claim 9, which is a dosage form suitable for oral administration.

12. The pharmaceutical composition according to claim 11, wherein said dosage form is selected from a tablet, and a capsule.

13. A process for the preparation of crystalline form II of N-benzoyl-staurosporine comprising:
    (a) providing a solution of N-benzoyl-staurosporine in a solvent;
    (b) contacting the solution with a second solvent to form a precipitate which is crystalline form II of N-benzoyl-staurosporine, which shows on X-ray diffraction a peak at an angle of refraction 2-theta (θ), of 8.7±0.2 degrees; and
    (c) isolating the precipitate.

14. The process according to claim 13, wherein the solvent is selected from benzyl alcohol, DMF, DMSO, acetic acid or PEG.

15. The process according to claim 13, wherein the second solvent is selected from ethanol, THF or a solution of ethanol in water.

16. The process according to claim 13, further comprising drying the isolated precipitate.

* * * * *